(12) United States Patent
Cabeca

(10) Patent No.: US 11,679,074 B2
(45) Date of Patent: Jun. 20, 2023

(54) TOPICAL CREAMS

(71) Applicant: GOLDEN ISLES MEDICAL INC., St. Simons Island, GA (US)

(72) Inventor: Anna Cabeca, St. Simons Island, GA (US)

(73) Assignee: GOLDEN ISLES MEDICAL INC., St. Simons Island, GA (US)

( * ) Notice: Subject to any disclaimer, the term of this patent is extended or adjusted under 35 U.S.C. 154(b) by 0 days.

(21) Appl. No.: 18/051,536

(22) Filed: Nov. 1, 2022

(65) Prior Publication Data

US 2023/0138716 A1    May 4, 2023

Related U.S. Application Data

(60) Provisional application No. 63/274,029, filed on Nov. 1, 2021.

(51) Int. Cl.
*A61K 36/00*  (2006.01)
*A61K 8/92*  (2006.01)
*A61K 8/63*  (2006.01)
*A61K 8/9789*  (2017.01)
*A61K 8/67*  (2006.01)
*A61K 8/34*  (2006.01)

(52) U.S. Cl.
CPC ............. *A61K 8/925* (2013.01); *A61K 8/342* (2013.01); *A61K 8/63* (2013.01); *A61K 8/678* (2013.01); *A61K 8/922* (2013.01); *A61K 8/9789* (2017.08)

(58) Field of Classification Search
CPC combination set(s) only.
See application file for complete search history.

(56) References Cited

U.S. PATENT DOCUMENTS

2010/0074963 A1 *  3/2010  Bettle .................. A61K 8/98
                                                          424/725

\* cited by examiner

*Primary Examiner* — Qiuwen Mi
(74) *Attorney, Agent, or Firm* — Polsinelli PC

(57) ABSTRACT

The present disclosure provides compositions as topical creams for treating vaginal atrophy, methods of making these compositions, and methods of using these compositions to treat vaginal atrophy.

17 Claims, No Drawings

TOPICAL CREAMS

CROSS-REFERENCE TO RELATED APPLICATION

This application claims benefit of U.S. Provisional Patent Application No. 63/274,029, which was filed in the U.S. Patent and Trademark Office on Nov. 1, 2021, the entire contents of which are incorporated herein by reference for all purposes.

FIELD OF THE DISCLOSURE

The present disclosure generally relates compositions as topical creams, methods of making these topical creams, and a method of treating vaginal discomfort or bladder control issues.

BACKGROUND OF THE INVENTION

Before menopause a woman's ovaries produce several different hormones including, but not limited to, estrogen. Estrogen is generally beneficial in maintaining the health and integrity of the vaginal lining. During peri-post menopause, women can experience a decline in hormone levels. The gradual decrease in hormone production causes vaginal lining shrinkage and drying due to the decrease in healthy secretions. The lining of the vagina can become less elastic and can thin, causing irritation and discomfort, also known as vaginal atrophy. Specifically, some seventy-five percent of women can experience discomfort including, but not limited to, thinning, irritation, painful intercourse, excessive dryness, increased bladder infections, loss of lactobacilli, increased vaginal pH, decreased vaginal flora, decreased desire and/or arousal, and pelvic prolapse symptoms.

Changes, as described above, can cause significant discomfort and pain. Therefore, there is a need for compositions and methods for reducing the discomfort and pain. Traditionally, such symptoms can be treated through the use of lubricating creams, as well as over-the-counter (OTC) treatments, herbal therapies, prescribed medication (such as vaginal tablets, creams, or rings), and Kegel/pelvic-strengthening exercise or surgery.

What is needed is a topical cream which relieves the symptoms of vaginal atrophy, is effective, easy to prepare, and has a long shelf life.

SUMMARY OF THE INVENTION

One aspect of the present disclosure relates to compositions as topical creams for treating vaginal discomfort bladder control issues. The compositions comprise: (a) from about 0.1 weight % (wt. %) to about 6.0 wt. % of at least one natural hormone; (b) from about 0.1 wt. % to 1.0 wt. % of at least one vitamin; (c) from about 10.0 wt. % to about 25.0 wt. % of at least one substance derived from a plant, an insect, or an animal; (d) from about 0.1 wt. % to about 1.0 wt. % of at least one botanical additive; (e) from about 1.0 wt. % to about 5.0 wt. % of one or more water soluble organic solvents; (f) from about 5.0 wt. % to about 15.0 wt. % of one or more fatty alcohols; and (g) from about 47.0 wt. % to about 83.7 wt. % water.

Another aspect of the present disclosure relates to methods of preparing a composition for use in treating vaginal discomfort or bladder control issues. The methods comprise: (a) adding water and heating to 50° C.; (b) contacting the at least one substance derived from a plant, an insect, or an animal and one or more fatty alcohols with the water forming a mixture; (c) contacting the at least one natural hormone and the one or more water soluble organic solvents with the mixture from step (b); (d) allowing the mixture from step (c) to cool to 25° C.; and (e) contacting the at least one vitamin and the at least one botanical additive with the cooled mixture from step (d).

Other features and iterations of the invention are described in more detail below.

DETAILED DESCRIPTION OF THE INVENTION

The present disclosure encompasses compositions as a topical cream, methods of making these compositions as a topical cream, and method of using these compositions as topical creams in treating a vaginal atrophy. Some of the prominent symptoms of vaginal atrophy are vaginal discomfort and/or bladder control issues.

I. Compositions

The present disclosure encompasses compositions as topical creams which are useful in treating vaginal atrophy. The compositions, as detailed herein, treat symptoms relating to vaginal atrophy such as vaginal discomfort or bladder control issues.

At Least One Natural Hormone

The composition includes at least one natural hormone. Suitable, non-limiting examples of natural hormones may be estrogen, selective estrogen receptor modulators (SERMs), androgens (such as androsterone, androstenedione (A4), androstenediol (A5), testosterone, dihydrotestosterone (DHT), dehydroepiandrosterone (DHEA), and dehydroepiandrosterone sulfate (DHEA-S), pregnenolone, progesterone, or combinations thereof. In one embodiment, the at least one natural hormone is dehydroepiandrosterone (DHEA).

Generally, the weight % (wt. %) of the at least one natural hormone may range from about 0.1 weight % (wt. %) to about 6.0 wt. %. In various embodiments, the wt. % of the at least one natural hormone may range from about 0.1 weight % (wt. %) to about 6.0 wt. %, from about 1.0 wt. % to about 4.0 wt. %, from about 1.0 wt. % to about 3.0 wt. %, from about 2.0 wt. % to about 4.0 wt. %. from about 3.0 wt. % to about 6.0 wt. %, from about 0.1 weight % (wt. %) to about 1.0 wt. %, from about 1.0 weight % (wt. %) to about 2.0 wt. %, from about 2.0 weight % (wt. %) to about 3.0 wt. %, from about 3.0 weight % (wt. %) to about 4.0 wt. %, from about 4.0 weight % (wt. %) to about 5.0 wt. %, or from about 5.0 wt. % to about 6.0 wt. %. In one embodiment, the wt. % of the at least one natural hormone ranges from 1.0 wt. % to about 4.0 wt. %.

At Least One Vitamin

The composition includes at least one vitamin. The at least one vitamin is designed to improve skin tone, improve skin cells, improve skin cell repair, cell repair, provide anti-oxidative properties, reduce irritation of the skin and skin cells, and reduce skin aging.

The at least one vitamin may be a vitamin useful in treating skin conditions may be a fat-soluble vitamin, a water-soluble vitamin, or combination thereof. Suitable, non-limiting examples of vitamins include vitamin A, vitamin B1, vitamin B2, vitamin B3, vitamin B5, vitamin B6, vitamin B7, vitamin B9, vitamin B12, vitamin C, vitamin D, vitamin E, vitamin K, folate, pyridoxine, thiamine, pantothenic acid, and biotin. The form of the vitamin may include salts of the vitamin, derivatives of the vitamin, compounds having the same or similar activity of a vitamin, and metabolite derivatives of a vitamin. In one embodiment, the at least one vitamin is vitamin E or a derivative of Vitamin E.

In general, the at least one vitamin may have a wt. % ranging from about 0.1 wt. % to about 1.0 wt. %. In various embodiments, the at least one vitamin may have a wt. % ranging from about 0.1 wt. % to about 1.0 wt. %, from about 0.1 wt. % to about 0.25 wt. %, from about 0.25 wt. % to about 0.5 wt. %, from about 0.5 wt. % to about 0.75 wt. %. from about 0.75 wt. % to about 1.0 wt. %, from about 0.1 wt. % to about 0.2 wt. %, from about 0.2 wt. % to about 0.3 wt. %, from about 0.3 wt. % to about 0.4 wt. %, from about 0.4 wt. % to about 0.5 wt. %, from about 0.5 wt. % to about 0.6 wt. %, from about 0.6 wt. % to about 0.7 wt. %, from about 0.7 wt. % to about 0.8 wt. %, from about 0.8 wt. % to about 0.9 wt. %, or from about 0.9 wt. % to about 1.0 wt. %. In one embodiment, the at least one vitamin has a wt. % ranging from 0.1 wt. % to about 0.5 wt. %.

At Least One Natural Substance Derived from a Plant, An Insect, or an Animal

The composition includes one natural substance derived from a plant, and insect, or an animal. These substances provide beneficial properties to the topical cream such as providing pleasing flavors and/or scents, reduce anxiety, reduce pain, and other benefits. These natural substances include but not limited to an essential oil, an oil, an extract, a gum, a wax, or a derivative of the natural substance. Suitable, non-limiting examples of these natural substances may be organic coconut oil, Ayurveda ghee, black cohosh, soy isoflavones, magnolia bark, alpine rose stem cells, emu oil, vitamin E tocopherol, shea butter, emu oil, botanical fillers, and the like. Maca, resveratrol, olive oil, pracaxi oil, cyclopentasiloxane, polysilicone-11, Macadamia glyceride, dimethicone, alkyl cetearyl dimethicone crosspolymer, petaclethra macroloba seed oil, oenocarpus bataua pulp oil, phosphatidylcholine, tocophyeryl acetate, BHT, aloe vera leaf, mineral oil, grapefruit seed extract, sodium benzoate, propylene glycol, xylitol, mung fruit extract, palm fruit oil, ethoxydiglycol, guarhydroxypropyltrimonium, chloride, hydroxyethylcellulose, citric acid, benzyl alcohol, methylisothiazolinone, and methylchloroisothiazolinone, magnesium stearate, dimethicone, dimethiconol, and cyclomethicone, hydroxyethylcellulose, gloconolactone, chlorhexidine digluconoate, Aloe barbadensis (Aloe Vera)*, Cyamopsis tetragonolobus (Guar Gum)*, Ceratonia siliqua (Locust Bean Gum)*, Linum usitatissimum (Flax extract)*, Xanthan Gum, Citric Acid, Potassium sorbate, Phenoxyethanol, Butyrospermum Parkii (Shea Butter)*, Prunus Dulcis (Sweet Almond Oil)*, Helianthus Annuus (Sunflower Oil)*, Theobroma Cacao (Cocoa Butter)*, Cera Alba (Bees Wax), linseed oil extract, acacia gum, gums from seaweeds, e.g. alginates or Carrageenan, Beta glucans, fruit gums, sunflower oil, avocado oil, pomegranate oil, cocoa butter, muscadine pomace, lavender essential oil, frankincense essential oil, bergamot essential oil, paraffin wax, propolis, natural oils and natural organic oils such as including vegetable oil, citrus oil, plant oil, fish oil, non-citric fruit oil, oils having flavors, perfume or scents, etc. Suitable vegetable oils may be canola oil, corn oil, neem oil, olive oil, cottonseed oil, coconut oil, palm oil, nut oils, safflower oil, sesame oil, soybean oil, and sunflower oil. Nut oils can be peanut oil, almond oil, cashew oil, hazelnut oil, macadamia oil, pecan oil, pine nut oil, pistachio oil, and walnut oil. Citrus oils can include grapefruit seed oil, lemon oil, orange oil, tangerine oil, lime oil, mandarin oil, and the like. Other oils based on fruits, plants and fish would include fish oil such as omega 3 oil, flaxseed oil (linseed oil), apricot oil, avocado oil, cocoa butter oil, coconut oil, hemp oil, papaya seed oil, rice bran oil, shea butter oil, tea tree seed oil, and wheat germ oil. Other oils can include lavender oil, rosemary oil, tung oil, jojoba oil, poppy seed oil, castor oil, mango oil, rose hip oil, tall oil. Essential oils can include chamomile oil, cinnamon oil, citronella oil, eucalyptus oil, fennel seed oil, jasmine oil, juniper berry oil, lavender oil, lemon grass oil, nutmeg oil, patchouli oil, peppermint oil, pine oil, rose oil, rose hip oil, rosemary oil, rosewood oil, sandalwood oil, sassafras oil, spearmint oil, and wintergreen oil. Waxes include beeswax, carnauba wax (palm wax), coconut wax and soy wax. Anti-oxidants like grape seed extract, curcumin; fractionated coconut oil, mangosteen, arginine. In one embodiment, the at least one natural substance is a mixture of coconut oil, emu oil, and shea butter.

Generally, the at least one natural substance derived from a plant, and insect, or an animal may have a wt. % ranging from about 10.0 wt. % to about 25.0 wt. %. In various embodiments, the at least one natural substance derived from a plant, and insect, or an animal may have a wt. % ranging from about 10.0 wt. % to about 25.0 wt. %, from about 10.0 wt. % to about 15.0 wt. %, from about 15.0 wt. % to about 20.0 wt. %, from about 20.0 wt. % to about 25.0 wt. %, from about 10.0 wt. % to about 12.5 wt. %, from about 12.5 wt. % to about 15.0 wt. %, from about 15.0 wt. % to about 17.5 wt. %, from about 17.5 wt. % to about 20.0 wt. %, from about 20.0 wt. % to about 22.5 wt. %, or from about 22.5 wt. % to about 25.0 wt. %. In one embodiment, the at least one natural substance derived from a plant, and insect, or an animal may have a wt. % ranging from about 15.0 wt. % to about 20.0 wt. %.

At Least One Botanical Substance

The composition includes at least one botanical substance. These botanical substances may be an extract from a plant and provide additional properties to the topical cream. Suitable, non-limiting examples of these botanical substances may be alpine rose stem cell extract, calendula flower extract, chamomile flower extract, damask rose flower extract, eucalyptus leaf extract, ginger root extract, Ginkgo biloba extract, gotu kola extract, green tea leaf extract, hibiscus flower extract, japanese honeysuckle flower extract, lavender flower extract, lemon balm extract, lemon peel extract, licorice root extract, marshmallow root extract, panax ginseng root extract, peony root extract, peppermint leaf extract, pomegranate extract, Provence rose flower extract, rosemary leaf extract, sag e leaf extract, vanilla bean extract, white tea leaf extract, white willow bark extract, or a combination thereof. In one embodiment, the at least one botanical substance is alpine rose stem cell extract.

In general, the at least one botanical substance may have a wt. % in the composition from about 0.1 wt. % to about 1.0 wt. %. In various embodiments, the at least one botanical substance may have a wt. % in the composition from about 0.1 wt. % to about 1.0 wt. %, from about 0.1 wt. % to about 0.2 wt. %, from about 0.2 wt. % to about 0.3 wt. %, from about 0.3 wt. % to about 0.4 wt. %, from about 0.4 wt. % to about 0.5 wt. %, from about 0.5 wt. % to about 0.6 wt. %, from about 0.6 wt. % to about 0.7 wt. %, from about 0.7 wt. % to about 0.8 wt. %, from about 0.8 wt. % to about 0.9 wt. %, or from about 0.9 wt. % to about 1.0 wt. %. In one embodiment, the at least one botanical substance may have a wt. % from about 0.1 wt. % to about 0.3 wt. %.

One or More Water Soluble Organic Solvent

The composition includes one or more water soluble organic solvents. Non-limiting examples of water-soluble solvents may be glycerin, $C_2$-$C_6$ mono-alcohols, polyols (polyhydric alcohols), glycols, and a mixture thereof. In one embodiment, the one or more water soluble organic solvent is glycerin.

Generally, the one or more water soluble organic solvent may have a weight % ranging from about 1.0 wt. % to about 5.0 wt. %. In various embodiments, the one or more water soluble organic solvent may have a weight % ranging from about 1.0 wt. % to about 5.0 wt. %, from about 1.0 wt. % to about 2.5 wt. %, from about 2.5 wt. % to about 5.0 wt. %, from about 1.0 wt. % to about 3.0 wt. %, from about 2.0 wt. % to about 4.0 wt. %, or from about 3.0 wt. % to about 5.0 wt. %. In one embodiment, the one or more water organic soluble solvent may have a weight % ranging from about 2.0 wt. % to about 4.0 wt. %.

One or More Fatty Alcohols

The composition includes one or more fatty alcohols. Non-limiting examples of one or more fatty alcohols may be decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl dodecanol, and a mixture thereof. In one embodiment, the one or more fatty alcohols is a mixture of cetearyl alcohol and undecyl alcohol.

In general, the one or more fatty alcohols may have a wt. % ranging from 5.0 wt. % to about 15.0 wt. %. In various embodiments, the one or more fatty alcohols may have a wt. % ranging from 5.0 wt. % to about 15.0 wt. %, from about 5.0 wt. % to about 7.5 wt. %, from about 7.5 wt. % to about 10.0 wt. %, from about 10.0 wt. % to about 12.5 wt. %, from about 12.5 wt. % to about 15.0 wt. %, from about 7.0 wt. % to about 12.0 wt. %, from about 7.0 wt. % to about 10.0 wt. %, from about 10.0 wt. % to about 13.0 wt. %, or from 13.0 wt. % to about 15.0 wt. %. In one embodiment, the one or more fatty alcohols may have a wt. % ranging from 7.0 wt. % to about 12.0 wt. %.

Water

The composition included water. Water is added in the amount as needed (q.s. or Q.S.). The water used in the composition may be distilled water, filtered water, purified water, deionized water, or a combination thereof.

Generally, the water used in the composition may have a wt. % ranging from about 47.0 wt. % to about 83.7 wt. %. In various embodiments, the water used in the composition may have a wt. % ranging from about 47.0 wt. % to about 83.7 wt. %, from about 47.0 wt. % to about 50.0 wt. %, from about 50.0 wt. % to about 60.0 wt. %, from about 60.0 wt. % to about 70.0 wt. %, from about 70.0 wt to about 80.0 wt. %, or from about 80.0 wt. % to about 83.7 wt. %. In one embodiment, the water used in the composition is added in the amount as needed, about 60 wt. % to about 70 wt. %.

Properties of the Composition

The composition provides some unique properties.

The composition is considered non-corrosive and do not cause damage to the skin or skin cells of a subject. The non-corrosive nature of the composition can be attributed to the pH which is considered neutral. In general, the pH of the composition ranges from 6.0 to 8.0. In various embodiments, the pH of the composition ranges from 6.0 to 8.0, from about 6.0 to 6.5, from about 6.5 to 7.0, from about 7.0 to about 7.5, or from 7.5 to 8.0. In one embodiment, the pH is considered neutral, about pH of 7.0.

In general, the composition has a viscosity ranging from 70,000 centipoise (CPS) to about 90,000 CPS. In various embodiments, the composition has a viscosity ranging from 70,000 CPS to about 90,000 CPS, from about 70,000 CPS to about 75,000 CPS, from about 75,000 CPS to about 80,000 CPS, from about 80,000 CPS to about 85,000 CPS, or from about 85,000 CPS to about 90,000 CPS.

Generally, the composition has a plate count less than 1000 ($10^3$). In various embodiments, the composition has a plate count less than 1000, less than 500, less than 250, less than 100, less than 50, less than 25, less than 10, or less than 1.

In general, the compositions have a total yeast and mold count less than 100 ($10^2$). In various embodiments, the compositions have a total yeast and mold count less than 100, less than 50, less than 25. Less than 10, less than 5, or less than 1.

The composition, as detailed above is a topical cream and is white to off white at 25° C. These compositions have a shelf life greater than 1 year.

II. Methods of Making a Composition for Use in Treating Vaginal Discomfort or Bladder Control Issues The present disclosure encompasses methods of making a composition for use in treating vaginal discomfort or bladder control issues. The methods comprise: (a) adding water and heating to 50° C.; (b) contacting the at least one substance derived from a plant, an insect, or an animal and the one or more fatty alcohols with the water forming a mixture; (c) contacting the at least one natural hormone and the one or more water soluble solvents with the mixture from step (b); (d) allowing the mixture from step (c) to cool to 25° C.; and (e) contacting the at least one vitamin and the at least one botanical additive with the cooled mixture from step (d). The methods may be conducted in a batch, semi-batch, or continuous manner.

Step (a)

Step (a) of the 5-step method comprises adding water and heating the water to 50° C.

Water is described in more detailed above in Section I.

Generally, Step (a) will be conducted at a temperature that ranges from about 25° C. to about 100° C. depending on the solvent utilized. In various embodiments, the temperature of Step (c) may range from about 25° C. to about 100° C., from about −25° C. to about 50° C., from about 50° C. to about 75° C., or from about 75° C. to about 100° C. In an embodiment, Step (a) is conducted at about 50° C.

Step (b)

The second step, Step (b) of the 5-step method comprises contacting the at least one substance derived from a plant, an insect, or an animal and the one or more fatty alcohols with the water forming a mixture. The at least one substance derived from a plant, an insect, or an animal and the one or more fatty alcohols and the amounts of these components are described in more detail above.

The at least one substance derived from a plant, an insect, or an animal and the one or more fatty alcohols are melted to a temperature ranging from 50° C. to 100° C. to ensure these components are liquid in nature. The components may be added in any sequential order, portion wise, or all at once after heating to the water. Once these components are added, these components are mixed until a homogeneous mixture is obtained. Various types of mixing are known in the art such as mechanical mixing.

Step (c)

The next step in the 5-step method comprises contacting the at least one natural hormone and the one or more water soluble organic solvents with the mixture from step (b). Again, the at least one natural hormone and the one or more water soluble organic solvents may be added in any sequential order, portion wise, or all at once. Once these components are added, these components are mixed until a homogeneous mixture is obtained. Various types of mixing are known in the art such as mechanical mixing.

Step (d)

The next step in the 5-step method comprises allowing the mixture from step (c) to cool to about 25° C. This step is important to maintain the properties of the at least one vitamin and the at least one natural hormone which will be added in the subsequent step.

Step (e)

The last step in the 5-step method comprises contacting the at least one vitamin and the at least one botanical additive with the cooled mixture from step (d). Addition of these components as the last step of the method ensures that the vitamin and the at least one botanical additive maintains their perspective properties and provide maximum benefit to the subject.

III. Method of Treating Vaginal Discomfort or Bladder Control Issues

The present disclosure encompasses methods of treating vaginal atrophy such as vaginal discomfort or bladder control issues. The method comprises applying the compositions detailed above to the area of interest on the subject in need thereof.

Composition

The composition as a topical cream, are described in more detail above.

Subject

The subject is a human female subject which is undergoing menopause or other hormonal fluctuations.

Application

The compositions as a topical cream are applied by applying the topical cream to the affected area of the subject.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the ranges, or the characteristics being described.

As used herein, the term "about" is used to provide flexibility to a numerical range endpoint by providing that a given value may be "a little above" or "a little below" the endpoint. For example, the endpoint may be within 10%, 8%, 5%, 3%, 2%, or 1% of the listed value. Further, for the sake of convenience and brevity, a numerical range of "about 50 mg/mL to about 80 mg/mL" should also be understood to provide support for the range of "50 mg/mL to 80 mg/mL." The endpoint may also be based on the variability allowed by an appropriate regulatory body, such as the FDA, USP, etc.

The present disclosure provides inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open-ended term, like "comprising" or "including," it is understood that direct support should be afforded also to "consisting essentially of" language as well as "consisting of" language as if stated explicitly and vice versa.

The term "vaginal atrophy" refers to the thinning, drying, and inflammation of the vaginal walls due to a lack of estrogen in the body.

As various changes could be made in the above-described methods without departing from the scope of the invention, it is intended that all matter contained in the above description and in the examples given below, shall be interpreted as illustrative and not in a limiting sense.

EXAMPLES

The following examples are provided to illustrate the subject matter of the present disclosure. The examples are not intended to limit the scope of the present disclosure and should not be so interpreted.

Example 1

The following compositions were prepared for use in treating vaginal discomfort or bladder control issues.

| Component | Concentration (Weight Percent, wt. %) |
| --- | --- |
| Dehydroepiandrosterone (DHEA) | 1.0 wt. % to 4.0 wt. % |
| Vitamin E | 0.1 wt. % to 0.5 wt. % |
| Coconut oil, Emu Oil, and Shea Butter | 15.0 wt. % to 20.0 wt. % |
| Glycerin | 2.0 wt. % to 4.0 wt. % |
| Cetearyl Alcohol and Undecyl Alcohol | 7.0 wt. % to 12.0 wt. %. |
| Alpine Rose Stem Cells | 0.3 wt. % to 0.7 wt. % |
| Water | q.s. |

What is claimed is:

1. A composition in the form of a cream for use in treating vaginal discomfort or bladder control issues, the composition comprises:
   a. from about 0.1 weight % (wt %) to about 6.0 wt. % of dehydroepiandrosterone (DHEA);
   b. from about 0.1 wt. % to 1.0 wt. % of at least one vitamin;
   c. from about 10.0 wt. % to about 25.0 wt. % of coconut oil, emu oil, and shea butter;
   d. from about 0.1 wt. % to about 1.0 wt. % of at least one botanical extract;
   e. from about 1.0 wt. % to about 5.0 wt. % of one or more water organic solvents;

f. from about 5.0 wt. % to about 15.0 wt. % of one or more fatty alcohols; and
g. from about 47.0 wt. % to about 83.7 wt. % water.

2. The composition of claim 1, wherein the weight % of dehydroepiandrosterone ranges from about 1.0 wt. % to about 4.0 wt. %.

3. The composition of claim 1, wherein the weight % of the at least one vitamin ranges from 0.1 wt. % to about 0.5 wt. %.

4. The composition of claim 1, wherein the weight % of the coconut oil, emu oil, and shea butter ranges from about 15.0 wt. % to about 20.0 wt. %.

5. The composition of claim 1, wherein the weight % of the at least one botanical extract ranges from about 0.3 wt. % to about 0.7 wt. %.

6. The composition of claim 1, wherein the weight % of one or more water soluble organic solvents ranges from about 2.0 wt. % to about 4.0 wt. %.

7. The composition of claim 1, wherein the weight % of one or more fatty alcohols ranges from about 7.0 wt. % to about 12.0 wt. %.

8. The composition of claim 1, wherein the composition has a pH ranging from about 6.0 to about 8.0.

9. The composition of claim 1, wherein the composition has a viscosity ranging from about 70,000 centipoises (CPS) to about 90,000 CPS.

10. The composition of claim 1, wherein total plate count is less than $10^3$.

11. The composition of claim 1, wherein the composition has a total yeast and mold count less than $10^2$.

12. The composition of claim 1, wherein the composition is a topical cream and is white or off white in color at 25° C.

13. A method of preparing a composition of claim 1 for use in treating vaginal discomfort or bladder control issues comprising:
   a. adding water and heating to 50° C.;
   b. contacting the coconut oil, emu oil, and shea butter and the one or more fatty alcohols in water forming a mixture;
   c. contacting the dehydroepiandrosterone and the one or more water soluble organic solvents with the mixture from step (b);
   d. allowing the mixture from step (c) to cool to 25° C.; and
   e. contacting the at least one vitamin and the at least one botanical extract with the cooled mixture from step (d).

14. A method of treating vaginal discomfort or bladder control issues, the method comprises applying the composition of claim 1 to a subject in need thereof.

15. The method of claim 14, wherein the subject is a female human.

16. The method of claim 15, wherein the female subject is undergoing menopause or other hormonal fluctuations.

17. The method of claim 14, wherein the method treats one or more symptoms comprising vulvar-vaginal thinning and irritation; painful intercourse due to excessive vaginal dryness; decreased normal flora, loss of lactobacilli and increased pH, leading to increased vaginal and bladder infections; leaking urine or loss of bladder control; increased skin disorders affecting the urogenital tract including vulvodynia, vestibulitis, hypertrophic dystrophy, dermatitis; decreased sexual desire, arousal, and orgasm; and pelvic prolapse symptoms including pressure on the bladder as well as difficulty in bladder elimination.

* * * * *